(12) United States Patent
Marsh et al.

(10) Patent No.: US 11,690,736 B2
(45) Date of Patent: Jul. 4, 2023

(54) ANTI-BACK DRIVE DEVICE

(71) Applicant: Hugh Steeper Limited, Leeds (GB)

(72) Inventors: Garry Marsh, Poole (GB); James Sykes, Leeds (GB)

(73) Assignee: Hugh Steeper Limited, Leeds (GB)

(*) Notice: Subject to any disclaimer, the term of this patent is extended or adjusted under 35 U.S.C. 154(b) by 260 days.

(21) Appl. No.: 16/951,097

(22) Filed: Nov. 18, 2020

(65) Prior Publication Data

US 2021/0154028 A1    May 27, 2021

(30) Foreign Application Priority Data

Nov. 25, 2019    (GB) .................................... 1917151

(51) Int. Cl.

| | |
|---|---|
| *A61F 2/70* | (2006.01) |
| *B25J 15/08* | (2006.01) |
| *F16H 35/00* | (2006.01) |
| *A61F 2/54* | (2006.01) |
| *A61F 2/58* | (2006.01) |
| *A61F 2/68* | (2006.01) |
| *A61F 2/50* | (2006.01) |

(52) U.S. Cl.
CPC ................ *A61F 2/70* (2013.01); *A61F 2/583* (2013.01); *A61F 2/586* (2013.01); *B25J 15/083* (2013.01); *A61F 2002/5067* (2013.01); *A61F 2002/5073* (2013.01); *A61F 2002/6836* (2013.01); *A61F 2002/6845* (2013.01); *A61F 2002/701* (2013.01); *F16H 2035/005* (2013.01)

(58) Field of Classification Search
CPC ................................................ F16H 2035/005
See application file for complete search history.

(56) References Cited

U.S. PATENT DOCUMENTS

| | | | |
|---|---|---|---|
| 1,529,248 | A | 3/1925 | Greene et al. |
| 5,752,590 | A | 5/1998 | Lin |
| 2015/0075936 | A1 | 3/2015 | Akiyoshi et al. |

FOREIGN PATENT DOCUMENTS

| | | |
|---|---|---|
| DE | 86 20 711 | 9/1987 |
| DE | 10 2017 120 466 | 8/2018 |
| EP | 1 101 967 | 5/2001 |
| EP | 1 199 490 | 4/2002 |
| EP | 1 691 100 | 8/2006 |
| EP | 3 106 698 | 12/2016 |
| FR | 2 889 491 | 2/2007 |

(Continued)

*Primary Examiner* — David H Willse
(74) *Attorney, Agent, or Firm* — Clark & Brody LP

(57) ABSTRACT

A rotary drive member drives a driven member. A ring surrounding the driven member has two cam recesses containing lock members between cam surfaces of cam recesses and the ring. Each recess accommodates an associated lock member at different locations where the recess is shallower. Driving the driven member is permitted in a given rotation relative to the ring, but each lock member inhibits rotation of the driven member in the opposite sense. The recesses extend in opposite directions. Coupling between the driven members is free-play whereby reversal in the rotation disengages members and reengages. Protuberances extending into cam recesses retain a lock member associated with one recess at the deeper location permitting movement of the other lock member towards the shallower location. Upon reversal of the rotation, the protuberances retain another lock member at the deeper location permitting movement of one lock member.

19 Claims, 3 Drawing Sheets

(56) References Cited

FOREIGN PATENT DOCUMENTS

| | | |
|---|---|---|
| FR | 2 917 022 | 12/2008 |
| GB | 409 251 | 4/1934 |
| GB | 1 355 937 | 6/1974 |
| GB | 2 205 617 | 12/1988 |
| WO | 2006/115343 | 11/2006 |
| WO | 2009/134437 | 11/2009 |
| WO | 2016/129587 | 8/2016 |

ANTI-BACK DRIVE DEVICE

The present invention relates to an anti-back drive device.

Such a device is especially but not exclusively useful for the operation of a prosthetic hand, for example to enable a grip to be maintained without the need for a clutch and dissipation of energy whilst an electric motor maintains the grip via the clutch.

An anti-back drive device is illustrated by and described with reference to FIG. 5 of GB 409,251. A disadvantage of such a drive is that it is only an anti-back drive in one sense of rotation of the drive.

The present invention seeks to obviate this disadvantage.

Accordingly, the present invention is directed to an anti-back drive device comprising a rotary drive member coupled to a rotary driven member to enable the rotary drive member to drive the rotary driven member, the device further comprising a ring which surrounds the rotary driven member, the rotary driven member being provided with at least two cam recesses on its periphery containing respective lock members between respective cam surfaces of the cam recesses and the said ring, each recess being sufficiently deep towards one of its ends to accommodate its associated lock member but not at locations towards its other end where the recess is shallower relative to the ring, whereby drive of the driven member by the drive member will be permitted by each lock member in a given sense of rotation of the driven member relative to the ring but each lock member will inhibit back drive rotation of the driven member in the opposite sense of rotation relative to the ring, characterised in that the said at least two cam recesses extend from their deeper to their shallower locations in opposite directions around the driven member, in that the coupling between the drive member and the driven member is a free-play coupling whereby a reversal in the sense of rotation of drive results in the disengagement of the coupling between those two members, a predetermined relative rotation between those two members in which they are disengaged from one another, and then re-engagement between them, and in that respective protuberances extend from the drive member into the said at least two cam recesses to retain one of the lock members associated with one of those recesses at the deeper location thereof whilst permitting movement of the other lock member towards the shallower location of its associated recess, and, upon reversal of the sense of rotation of the driven member by the drive member, to retain the said other of the said lock members at the deeper location of its associated recess whilst permitting movement of the said one of the lock members towards the shallower location of its association recess, so that the device is a bi-directional anti-back drive device.

The device may further comprise respective plungers seated in respective radially extending faces of the cam recesses which plungers are acted upon by resilient parts to urge the lock members towards the shallower locations of the recesses.

This provides the advantage of a rapid locking action in the event of back drive of the driven member.

Each lock member may comprise a roller member.

This further increases a rapid locking action in the event of back drive of the driven member and decreases frictional contact between the ring and the lock members.

Each cam surface may lie on an imaginary chord of an imaginary circle defined by the ring.

Such a surface is relatively easy to generate.

The said protuberances may comprise respective pins extending into the recesses in an axial direction of the device, as defined by the axis of rotation thereof.

Such protuberances are relatively easy to manufacture and fix relative to the drive member.

The pins may extend within holes provided in the drive member to enable the pins to be held therewithin.

The pins may be rotatable about their longitudinal axes.

This reduces their resistance to rotation of the roller members when they are in contact therewith.

The free-play coupling may comprise at least one further protuberance extending from the drive member into a slot in the driven member.

This enables disengagement between the drive member and the driven member when the sense of rotation of the drive member changes as the protuberance shifts from one end of the slot to the other, providing a relatively simple form of construction of the free-play coupling.

The slot may be arcuate.

This may enable the size of the slot to be less than it would have to be if for example it were straight.

The said at least one further protuberance may comprise a pin.

This is also a relatively simple form of construction that is relatively easy to manufacture.

The said protuberances may be further from the central axis of the device than the said at least one further protuberance.

This facilitates a more efficient action of the device.

The pin which constitutes the further protuberance may extend through an associated hole in the drive member.

The rotary driven member may be provided with four such cam recesses spaced apart around its periphery, any and every two successive ones of those recesses progressing in a given sense around the periphery extending from their deeper to their shallower locations in opposite directions around the periphery.

This gives a balanced application of forces when the device is in use.

The drive member may comprise a plate.

This gives a compact form of construction.

The driven member may comprise a plate.

This also provides for a compact construction.

The drive member may be circular, matching the size of the ring.

This facilitates a compact and well balanced construction.

The drive member may comprise a gear with teeth around its periphery.

This provides for an economy of parts.

The driven member may be circular.

This facilitates a compact and well balanced construction.

The present invention extends to a prosthesis having an anti-back drive device embodying the present invention.

An example of an anti-back drive device embodying the present invention, and a hand prosthesis having such a drive device, will now be described in greater detail with reference to the accompanying drawings, in which:—

Figure 1:
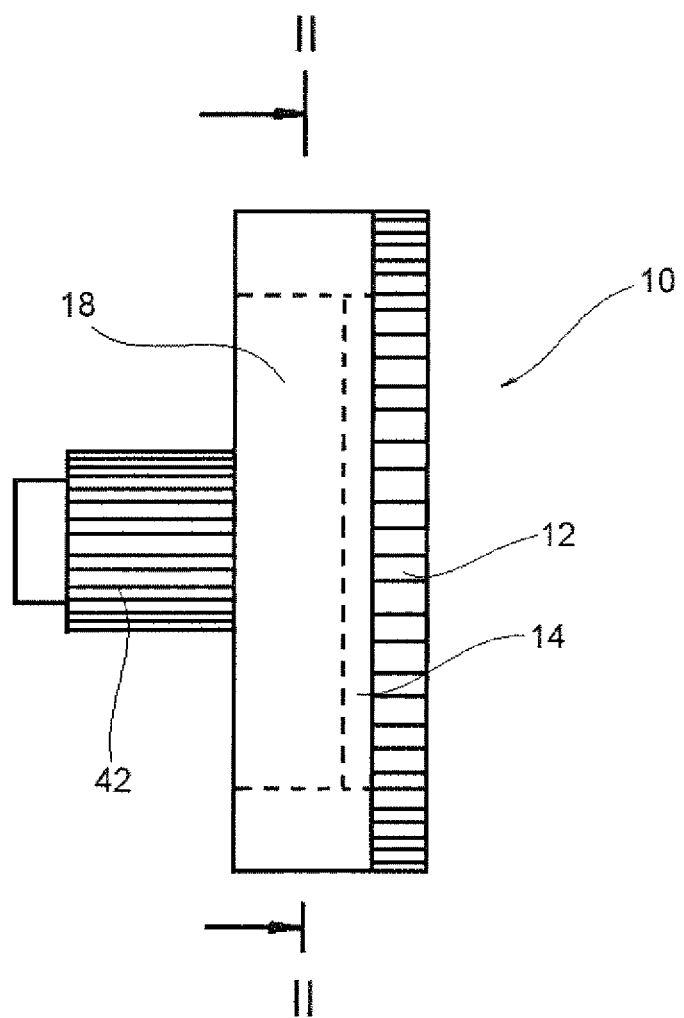
FIG. 1 is a side view of an anti-back drive device embodying the present invention.
Figure 2:
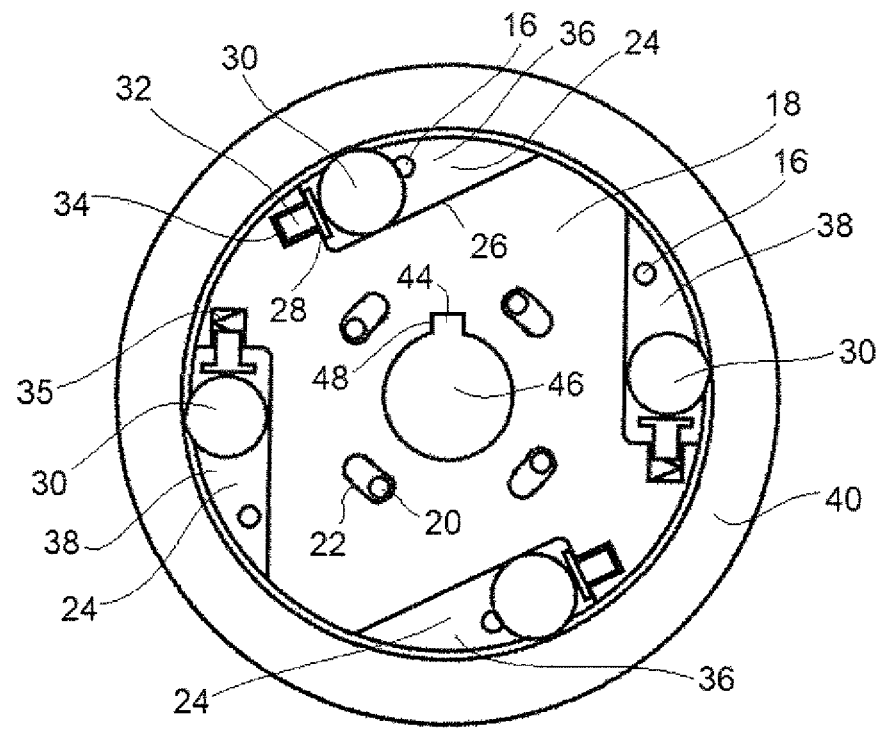
FIG. 2 is a cross-sectional view of the anti-back drive device shown in FIG. 1 taken in the plane indicated by the line II-II in FIG. 1, in a first configuration of the parts thereof.
Figure 3:
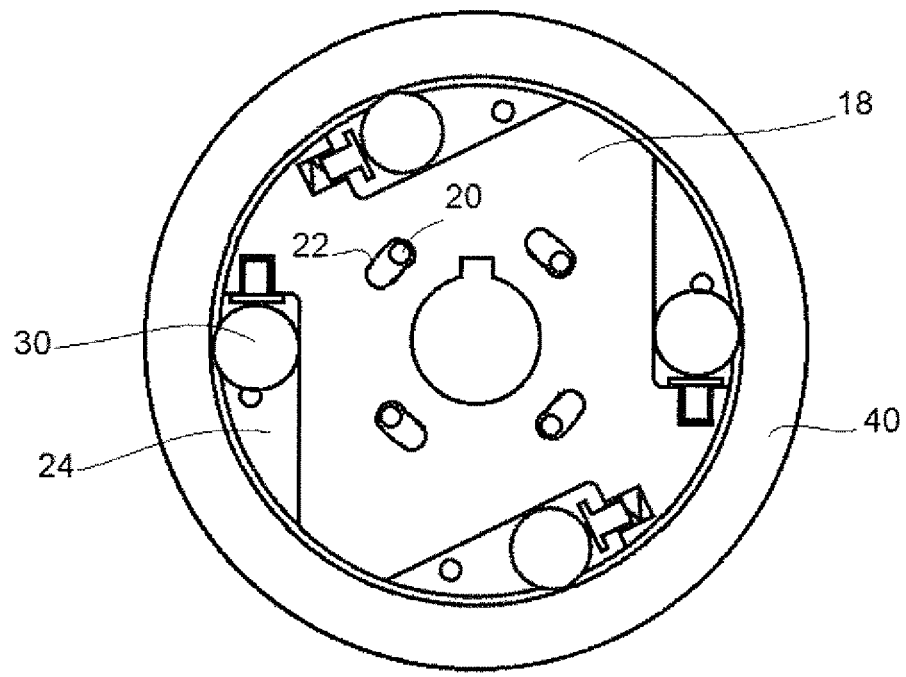
FIG. 3 is a cross-sectional view of the anti-back drive device shown in FIG. 1 taken in the plane indicated by the line in FIG. 1, in a second configuration of the parts thereof.

FIGS. 1 to 3 show an anti-back drive device 10 comprising a drive gear wheel 12 in the form of a plate constituting a drive member with gear teeth around its periphery and a circular protruding drive portion 14 within its outer periphery. Four pins 16 extend through respective through-holes (not shown) in and spaced circumferentially around the drive portion 14 generally perpendicularly to the drive gear wheel 12.

The drive portion 14 is coupled to a driven member constituted by a circular driven plate 18 by means of four pins 20 received in respective holes (not shown) in the drive portion 14 and extending in an axial direction into respective slots 22 in the driven plate 18 which are spaced apart uniformly therearound. The length of each slot 22 is slightly more than double the diameter of each pin 20.

The driven plate 18 is provided with four cam recesses 24 spaced apart around its circumference. Each recess is bounded on one side by a cam surface 26 constituted by a planar surface which, as viewed in FIGS. 2 and 3, lies on an imaginary chord of an imaginary circle defined by the outer circumference of the driven plate 18, with that part of the chord having one end lying on that circumference, and the other end being offset from the centre of the imaginary chord in the direction further from the end which lies on the circumference. A further planar bounding surface 28 of each recess 24 extends from the said other end of the said part of the chord to the circumference of the driven plate 18, perpendicularly to, or at least transversely of, the cam surface 26.

Respective roller members 30 are provided in the cam recesses 24 with their roller axes parallel to the axis of the device 10. Each roller member 30 is accommodated within locations towards the deeper end of its associated cam recess 24, but will not fit within locations towards the shallower end thereof. Each roller member 30 is in contact with a plunger 32 seated within a plunger recess 34 extending inwardly from and perpendicularly to the said further planar bounding surface 28 of the associated cam recess 24. A resilient spring 35 is provided within each plunger recess 34 to urge the plunger 32 towards its associated roller member 30. In FIGS. 2 and 3 each roller member 30 is at a location close to the deeper end of its associated cam recess 24, so that it is accommodated by the cam recess 24 and is free to roll.

A first pair 36 of the cam recesses 24 are located diametrically opposite one another and have their shallower ends displaced from their deeper ends in a clockwise direction around the circumference of the driven plate 18. The remaining pair 38 of the cam recesses 24 are also located diametrically opposite one another, but with their shallower ends displaced from their deeper ends in an anticlockwise direction around the circumference of the driven plate 18, and with the cam recesses 24 alternating from one pair to the other progressing around the circumference of the driven plate 18.

The driven plate 18 is surrounded by a ring 40 with the circumference of the driven plate 18 being concentric with but of slightly smaller radius than the inner surface of the ring 40, so that each roller member 30 lies between that inner surface and its associated cam surface 26, and so that each cam surface 26 also lies on an imaginary chord of an imaginary circle defined by the inner surface of the ring 40.

The pins 16 extend from the drive portion 14 into respective ones of the cam recesses 24. Two of them are located so as to hold their associated roller members 30 against their associated plungers 32 with the latter being depressed into their respective plunger recesses 34, and the other two are spaced away from their associated roller members 30 so that the associated plungers 32 extend a little out of their respective recesses 34.

A driven gear wheel 42 coaxial with the drive gear wheel 12 is rotationally fixed relative to the driven plate 18 by means of a key 44 on an axle 46 fixed to the driven gear wheel 42, which key 44 is engaged within a keyway 48 in the driven plate 18. The drive portion 14 and the drive gear wheel 12 can freely rotate about the axle 46.

In the relative configuration of the different parts of the device 10 shown in FIG. 2, the pins 20 abut the ends of their associated slots 22 which are displaced from their other ends in an anticlockwise sense around the driven plate 18, so that viewing the driven plate 18 as in FIG. 2, it is set to be driven by the drive portion 14 in an anticlockwise sense. In this configuration, the pins 16 of the pair 36 of cam recesses 24 abut their respective roller members 30, and the pins 16 of the pair 38 have their associated pins 16 spaced away from their respective roller members 30. As the drive portion 14 drives the driven plate 18 in an anticlockwise direction, the roller members 30 of the pair 38 are urged by any contact with the ring 40 up against their associated plungers 32, so that the latter push their roller members around the ring 40 so that they remain within the deeper portions of their associated cam recesses 24 and are free to rotate. The roller members 30 of the other pair 36 are held firmly against their respective plungers 32 at the deeper ends of the associated cam recesses by their associated pins 16, and are also therefore free to rotate. This condition may be referred to as "driving forwards". However, in the event that rotation stops, and then a back drive acts on the driven member 18 in the clockwise sense, the roller members 30 of the pair 38 of cam recesses 24 are free to roll along their respective cam surfaces 26 towards the shallower ends of those cam recesses 24. Since they are already close to a location along their cam surfaces 26 in which there is insufficient space to accommodate them, by virtue of the plungers 32 acted upon by the springs 35, they almost immediately become pinched between the inner surface of the ring 40 and their associated cam surfaces 26, so that they jam the driven plate 18 against rotation in the clockwise sense, and the device is effective as an anti-back drive against back drive of the driven plate 18 in this sense of rotation. This condition may be referred to as "backdriving forwards".

If the sense of rotation of the drive portion 14 is now reversed, the pins 20 which are fixed relative to the drive portion 14 shift to the opposite ends of their respective slots 22 as shown in FIG. 3. Thus the coupling between the drive portion 14 and the driven plate 18 is a free-play coupling, whereby this reversal in the sense of rotation of drive of the driven plate 18 by the drive portion 14 results in a disengagement of the coupling between those two parts as the pins 20 leave contact with respective ends of their respective slots 22, a predetermined relative rotation between those two parts as the pins 20 move towards the other ends of those slots so that the drive portion 14 and the driven plate are disengaged from one another, and then a re-engagement between them as the pins 20 abut the other ends of their respective slots 22. Because the pins 16 are also fixed relative to the drive portion 14, the roles of the pins 16 of the first pair 36 of cam recesses 24 are reversed with those of the second pair 38. This condition may be referred to as "driving backwards", and the device now acts as an anti-back drive against back drive of the driven member 18 in the anticlockwise sense. Should there be forces which now urge the driven member 18 in the anticlockwise sense, they will be countered by the construction of the device. Such a condition may be referred to as "backdriving backwards". Thus the device 10 acts as a bi-directional anti-back drive.

Figure 4:
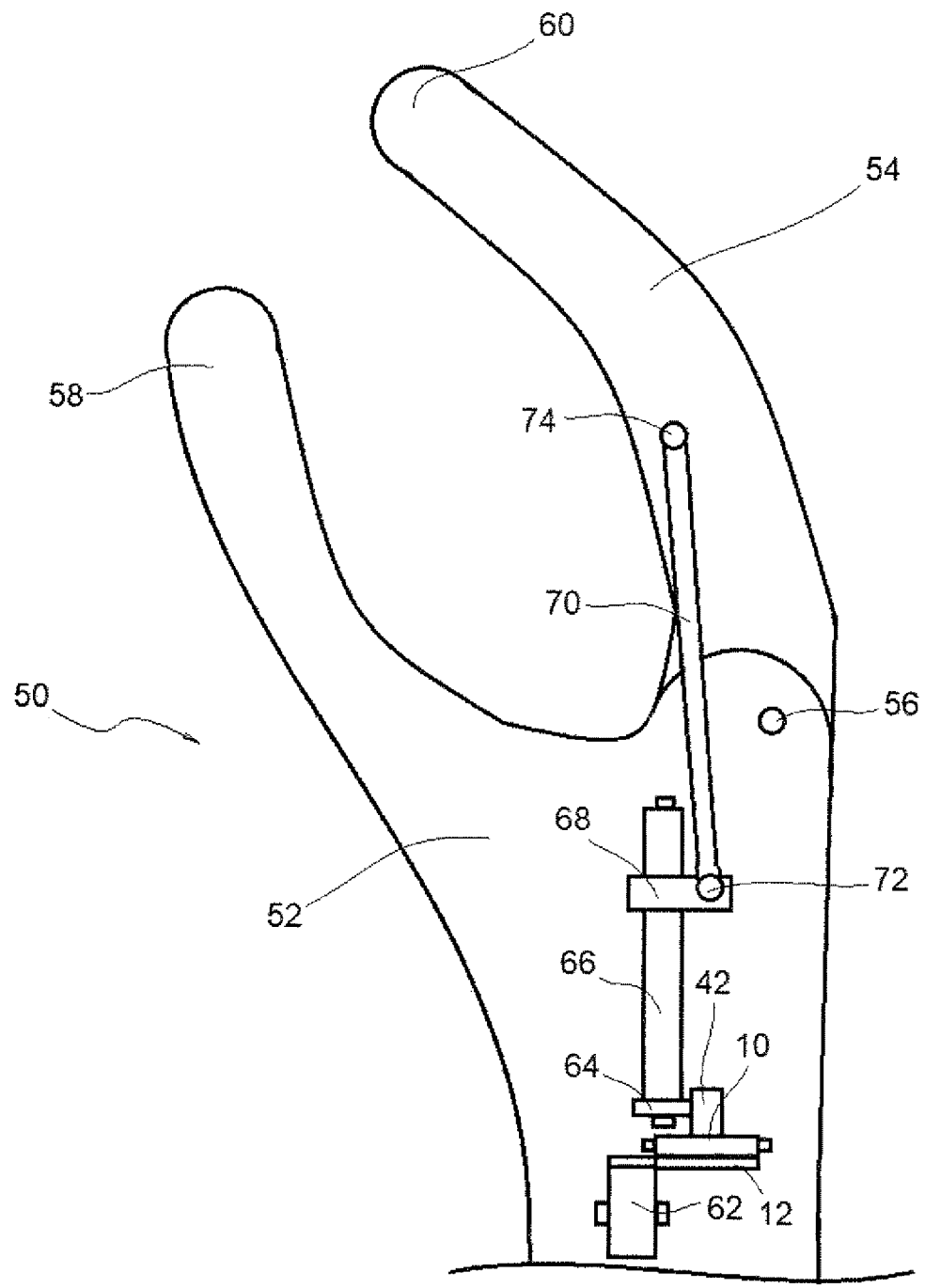
FIG. 4 is a diagrammatic view of a hand prosthesis provided with the anti-back drive device as shown in FIGS. 1 to 3.

FIG. 4 shows a simple hand prosthesis 50 fitted with an anti-back drive 10 as shown in FIGS. 1 to 3. The hand prosthesis comprises a fixed wrist and thumb part 52 with a finger part 54 coupled to the wrist and thumb part 52 by way of a pivot 56, so that the finger part 54 can pivot relative to the wrist and thumb part 52 about the pivot 56, to move respective ends 58 and 60 of the thumb and wrist part 52 and the finger part 54 towards or away from one another. An electric motor 62 is held within the wrist of the wrist and thumb part 52 and is coupled to drive the drive gear 12 of the anti-back drive device 10. The driven gear 42 thereof engages a gear 64 of a screwthreaded spindle 66 having a nut 68 which is moved up and down the spindle 66 according to the sense of rotation thereof. A rod 70 is connected by respective pivots 72 and 74 to the nut 68 and the finger part 54 at a position spaced from the pivot 56. According to the sense of rotation motor 62, and consequently the anti-back drive 10 and the spindle 66, the nut 68 will move up or down the spindle 66 to rotate the finger part 54 and hence adjust the spacing between the ends 58 and 60. Such a movement may therefore be used for an amputee who is wearing the prosthesis to take hold of an object, and then to stop operation of the motor without losing hold of the object because of the action of the anti-back drive device 10. The manner in which the amputee can operate such a prosthesis is well known to those familiar with the art and will not therefore be described in detail here, save to say that one method is by way of a myoelectric sensor (not shown).

It will be appreciated that a relative positioning between the drive portion 14 and the driven plate 18 half-way between the positionings shown in FIGS. 2 and 3 respectively, constitutes a neutral drive position in which no drive is occurring.

Numerous variations in the construction of the illustrated device may occur to the reader without taking the resulting construction outside the scope of the present invention. For example there may be more than four cam recesses 24 with associated roller members 30 and other parts. The roller members 30 might be replaced by wedge parts (not shown) as alternative lock members. The plungers 32, plunger recesses 34 and springs 35 may be omitted, although it is then preferable for the surface 28 to be so located as to provide very little movement available to the roller member 30 along the cam surface 26. Whilst the surfaces of the roller members 30 and the inner surface of the ring 40 are preferably plain, they may be textured or compliant surfaces. Plain solid roller members are preferred which resist wear and compression, but hollow roller members 30 with some degree of compliance may suit some applications. The device 10 may be provided with sensors (not shown) to supervise its operation, drive forces and mechanical states being controlled, modified, displayed and/or recorded, and/or signals from the sensors being transmitted to other parts of a system (not shown) of which the device forms a part. Instead of a key 44 and keyway 48 to lock the driven gear wheel 42 rotationally relative to the driven plate 18, a locking pin (not shown) may be provided which extends through through-holes (not shown) in the driven gear wheel 42 and in the driven plate 18.

We claim:

1. An anti-back drive device comprising a rotary drive member coupled to a rotary driven member to enable the rotary drive member to drive the rotary driven member, the device further comprising a ring which surrounds the rotary driven member, the rotary driven member being provided with at least two cam recesses on its periphery containing respective lock members between respective cam surfaces of the cam recesses and the said ring, each recess being sufficiently deep towards one of its ends to accommodate its associated lock member but not at locations towards its other end where the recess is shallower relative to the ring, whereby drive of the driven member by the drive member will be permitted by each lock member in a given sense of rotation of the driven member relative to the ring but each lock member will inhibit back drive rotation of the driven member in the opposite sense of rotation relative to the ring, wherein the said at least two cam recesses extend from their deeper to their shallower locations in opposite directions around the driven member, wherein the coupling between the drive member and the driven member is a free-play coupling whereby a reversal in the sense of rotation of drive results in the disengagement of the coupling between those two members, a predetermined relative rotation between those two members in which they are disengaged from one another, and then re-engagement between them, and wherein respective protuberances extend from the drive member into the said at least two cam recesses to retain one of the lock members associated with one of those recesses at the deeper location thereof whilst permitting movement of the other lock member towards the shallower location of its associated recess, and, upon reversal of the sense of rotation of the driven member by the drive member, to retain the said other of the said lock members at the deeper location of its associated recess whilst permitting movement of the said one of the lock members towards the shallower location of its associated recess, so that the device is a bi-directional anti-back drive device.

2. The anti-back drive device according to claim 1, wherein the device further comprises respective plungers seated in respective radially extending faces of the cam recesses which plungers are acted upon by resilient parts to urge the lock members towards the shallower locations of the recesses.

3. The anti-back drive device according to claim 1, wherein each lock member comprises a roller member.

4. The anti-back drive device according to any claim 1, wherein each cam surface lies on an imaginary chord of an imaginary circle defined by the ring.

5. The anti-back drive device according to any claim 1, wherein the said protuberances comprise respective pins extending into the recesses in an axial direction of the device, as defined by the axis of rotation thereof.

6. The anti-back drive device according to claim 5, wherein the pins extend within holes provided in the drive member to enable the pins to be held therewithin.

7. The anti-back drive device according to claim 5, wherein the pins are rotatable about their longitudinal axes.

8. The anti-back drive device according to claim 1, wherein the free-play coupling comprises at least one further protuberance extending from the drive member into a slot in the driven member.

9. The anti-back drive device according to claim 8, wherein the slot is arcuate.

10. The anti-back drive device according to claim 8, wherein the said at least one further protuberance comprises a pin.

11. The anti-back drive device according to claim 10, wherein the pin which constitutes the further protuberance extends through an associated hole in the drive member.

12. The anti-back drive device according to claim 8, wherein the said protuberances are further from a central axis of the device than the said at least one further protuberance.

13. The anti-back drive device according to claim 1, wherein the rotary driven member is provided with four such cam recesses spaced apart around its periphery, every two successive ones of those recesses progressing in a given sense around the periphery extending from their deeper to their shallower locations in opposite directions around the periphery.

14. The anti-back drive device according to claim 1, wherein the drive member comprises a plate.

15. The anti-back drive device according to claim 1, wherein the driven member comprises a plate.

16. The anti-back drive device according claim 1, wherein the drive member is circular, matching the size of the ring.

17. The anti-back drive device according claim 1, wherein the drive member comprises a gear with teeth around its periphery.

18. The anti-back drive device according to claim 1, wherein the driven member is circular.

19. A prosthesis having the anti-back drive device as claimed in claim 1.

* * * * *